(12) United States Patent
Nordhoff et al.

(10) Patent No.: US 7,557,246 B2
(45) Date of Patent: Jul. 7, 2009

(54) METHOD FOR THE PURIFICATION OF (METH)ACRYLIC ACID

(75) Inventors: Stefan Nordhoff, Recklinghausen (DE); Torsten Balduf, Houston, TX (US); Jürgen Mosler, Castrop-Rauxel (DE); Wilfried Uhlich, Marl (DE); Dennis Thong Yu-Chiang, Marl (DE); Axel Kobus, Langen (DE); Arndt Selbach, Marl (DE); Jürgen Kohn, Rheinberg (DE)

(73) Assignee: Evonik Stockhausen GmbH, Krefeld (DE)

( * ) Notice: Subject to any disclaimer, the term of this patent is extended or adjusted under 35 U.S.C. 154(b) by 0 days.

(21) Appl. No.: 11/571,877

(22) PCT Filed: Jul. 15, 2005

(86) PCT No.: PCT/EP2005/007719

§ 371 (c)(1),
(2), (4) Date: Jul. 5, 2007

(87) PCT Pub. No.: WO2006/008083

PCT Pub. Date: Jan. 26, 2006

(65) Prior Publication Data

US 2008/0091048 A1    Apr. 17, 2008

(30) Foreign Application Priority Data

Jul. 15, 2004    (DE) .................. 10 2004 034 316

(51) Int. Cl.
*C07C 51/42* (2006.01)
(52) U.S. Cl. .................................... 562/600
(58) Field of Classification Search ............... None
See application file for complete search history.

(56) References Cited

U.S. PATENT DOCUMENTS

| 5,504,247 | A | 4/1996 | Saxer et al. |
| 6,448,439 | B1 | 9/2002 | Eck et al. |

(Continued)

FOREIGN PATENT DOCUMENTS

DE    10149353 A1    7/2002

(Continued)

OTHER PUBLICATIONS

Translation of the International Preliminary Report on Patentability mailed on Nov. 27, 2006 in PCT/EP2005/007719.

(Continued)

*Primary Examiner*—Karl J Puttlitz
(74) *Attorney, Agent, or Firm*—Smith Moore Leatherwood LLP

(57) ABSTRACT

The present invention relates to a process for production of (meth)acrylic acid, whereby first a crude (meth)acrylic acid is produced and this crude (meth)acrylic acid is then continuously purified, whereby the continuous purification of the crude (meth)acrylic acid comprises the following process steps: a) in a composition comprising (meth)acrylic acid and impurities, precipitating the impurities in crystalline form from the composition; and b) separating the crystalline impurities precipitated from the composition. The invention also relates to the (meth)acrylic acid obtainable by this process, a device for production of (meth)acrylic acid, the use of the device or of a purification device for production of (meth)acrylic acid, (meth)acrylic acid, water-absorbing polymers, the use of water-absorbing polymers as well as fibers, sheets, foams and composites.

4 Claims, 4 Drawing Sheets

U.S. PATENT DOCUMENTS

| | | |
|---|---|---|
| 6,664,419 B1 * | 12/2003 | Bub .................... 562/600 |
| 2004/0116741 A1 | 6/2004 | Nordhoff et al. |
| 2004/0236049 A1 | 11/2004 | Fuchs et al. |
| 2005/0222459 A1 | 10/2005 | Nordhoff et al. |
| 2006/0013748 A1 | 1/2006 | Nordhoff et al. |

FOREIGN PATENT DOCUMENTS

| | | |
|---|---|---|
| DE | 10221202 A1 | 7/2003 |
| DE | 10211686 A1 | 10/2003 |
| DE | 10242746 A1 | 3/2004 |
| EP | 0616998 A1 | 9/1994 |
| WO | 9914181 A1 | 3/1999 |
| WO | 0045928 A1 | 8/2000 |
| WO | 03014172 A2 | 2/2003 |

OTHER PUBLICATIONS

International Search Report mailed on Nov. 22, 2005 in PCT/EP2005/007719.

* cited by examiner

US 7,557,246 B2

METHOD FOR THE PURIFICATION OF (METH)ACRYLIC ACID

This application is a national stage application under 35 U.S.C. 371 of international application No. PCT/EP2005/007719 filed Jul. 15, 2005, and claims priority to German Application No. DE 10 2004 034 316.0 filed Jul. 15, 2004, the disclosure of which is expressly incorporated herein by reference.

BACKGROUND OF THE INVENTION

The present invention relates to a process for production of (meth)acrylic acid, the (meth)acrylic acid obtainable by this process, a device for production of (meth)acrylic acid, the use of the device or of a purification device for the production of (meth)acrylic acid, (meth)acrylic acid, water-absorbing polymers, the use of water-absorbing polymers and fibers, sheets, foams and composites.

"(Meth)acrylic acid" is used in this text for the compounds with the nomenclature names "methacrylic acid" and "acrylic acid". Of the two compounds, acrylic acid is exemplary both in connection with the process according to the invention as well as in connection with the chemical products according to the invention.

Chemical starting products and intermediate products, in particular starting products for polymer production, are currently produced in very large amounts. In order to satisfy increasing demands on quality, these products may contain practically no impurities. This is particularly the case for acrylic acid, if it is to be used for the production of water-absorbing polymers, which are, for example, used in hygiene articles. Impurities in the acrylic acid influence disadvantageously its polymerization. Thus, with increasing amount of impurity in the acrylic acid, not only the portion of residual monomers in the acrylic acid polymers increases, but also the absorption behavior of the water-absorbing polymers based on acrylic acid is disadvantageously influenced by impurities in the acrylic acid used.

Acrylic acid is commonly obtained by catalytic gas phase oxidation of propylene with an oxygen-containing gas. In this way, in a two-step process, the propylene is first oxidized catalytically to acrolein, which is then converted to acrylic acid in a second process step, likewise using catalysts. The thus-obtained acrylic acid is removed in the form of an aqueous solution from the gaseous reaction mixture by absorption with water. The water in the thus-obtained aqueous acrylic acid is then separated with formation of a crude acrylic acid, by distillation, for example by means of an entrainer, whereby an acrylic acid-comprising bottom product (i.e., crude acrylic acid) is obtained.

Methacrylic acid can be produced analogously to acrylic acid, likewise by catalytic gas phase oxidation, whereby in this case, $C_4$-starting compounds, such as, for example, isobutene, isobutane, tert-butanol or methacrolein are used. The purification of the methacrylic acid obtained by the catalytic gas phase oxidation of $C_4$-starting compounds comprises, as for the purification of acrylic acid, the absorption of the methacrylic acid in a suitable solvent and the subsequent separation of the solvent whereby in this case, a crude methacrylic acid is obtained.

Since both in the catalytic gas phase oxidation of the $C_3$ or $C_4$ starting compounds, besides the acrylic acid or the methacrylic acid, other oxidation products are also formed, such as, for example, maleic acid anhydride, which, in the case of the production of water-absorbing polymers based on polyacrylates, can inhibit the polymerization and have a disadvantageous effect on the absorption properties of the water-absorbing polymers, a further purification of the crude (meth)acrylic acid is necessary. The purification of the crude (meth)acrylic acid occurs by means of purification processes known from the prior art, for example, by means of distillation of crystallization, whereby in the case of crystallization, it is technically differentiated between the two processes of suspension crystallization and layer crystallization (Wintermantel et al., Chem. Ing. Tech. 1991, 63, 881-891; Steiner et al., Chem. Ing. Tech. 1985, 57, 91-102).

Crystallization has the advantage over distillation that impurities, which cannot be removed by distillation, can often be separated by means of crystallization. Furthermore, crystallization can be carried out at considerably lower temperatures in comparison to distillation, so that the extent of formation of (meth)acrylic acid dimers or (meth)acrylic acid oligomers during the purification process can be reduced. Crystallization has, however, the disadvantage that impurities, which may be present in the melt, in particular fumaric acid, maleic acid and maleic acid anhydride, also precipitate on crystallization. Since the mother liquor or the melt is depleted in (meth)acrylic acid during the crystallization, impurities in the mother liquor are constantly enriched. As soon as the solubility limit is reached, these compounds precipitate from the mother liquor in crystalline form. In the case of a static layer crystallization, these undesired crystals form on the floor or the walls of a crystallizer. Since the crystals stick to the surface, these impurities remain in the crystallizer when the uncrystallized melt is discharged. If the separated crystal layer is then melted, whereby commonly two or more fractions are formed, the precipitated crystalline impurities which are still present on the floor and on the walls of the crystallizer are again taken up by the warmed melt. The result of this is that these impurities can never be completely removed and concentrate in the crystallizer. In a large-scale purification plant, in the course of a day, considerable amounts of impurities, such as, for example, maleic acid, can accumulate, which can block the conduits and valves of the purification device for (meth)acrylic acid. Impurities can also condense as a solid coating on the crystallizer walls or on the floor. These deposits not only lead to blockages, but also effect a reduction of the capacity of a plant for purification of (meth)acrylic acid, since a considerable amount of the volume, for example of the tanks situated in the plant, is taken up by the precipitated crystals.

It has thus become a necessity to separate the deposits.

To this end, WO-A-00/45928 proposes to prevent the precipitation of impurities in the purification process for acrylic acid, by addition of a solvent or a solvent mixture, whereby the solvent or the solvent mixture is added in such an amount that the impurities are held in solution. Water may be used as solvent. The disadvantage of this process is, however, that maleic acid and maleic acid anhydride are not separated by this process from the mother liquor, but constantly enrich in the mother liquor. The dilution of the mother liquor with solvent or the solvent mixture has, in addition, the result that in subsequently attached crystallizers, a crystallization of the acrylic acid is made more difficult by the introduction of a solvent.

One aspect of the present invention is to provide a process with which the disadvantages described in the prior art could be overcome.

Another aspect of the present invention is to provide a process for production of (meth)acrylic acid, which comprises a purification process for (meth)acrylic acid, in which impurities, in particular fumaric acid, maleic acid or maleic acid anhydride, can be separated in a simple way, without making more difficult a subsequent crystallization of the (meth)acrylic acid.

A further aspect of the present invention is to provide a (meth)acrylic acid, which, in comparison with the (meth) acrylic acid described in the prior art, is characterized by a particularly low content in impurities, such as, for example, fumaric acid, maleic acid or maleic acid anhydride.

An additional aspect of the present invention is to provide water-absorbing polymers, which are characterized by a particularly low content in impurities, such as, for example, fumaric acid, maleic acid or maleic acid anhydride, and thus by a particularly advantageous skin tolerance.

DETAILED DESCRIPTION OF THE PRESENT INVENTION

These objects are solved by a process for production of (meth)acrylic acid, whereby first a crude (meth)acrylic acid is prepared and this crude (meth)acrylic acid is then, in one aspect, continuously purified, whereby the continuous purification of the crude (meth)acrylic acid comprises the following process steps:
a) in a composition comprising (meth)acrylic acid and impurities, the impurities are precipitated in crystalline form from the composition;
b) the crystalline impurities precipitated from the composition are separated.

In one embodiment of the process according to the invention, the impurity is maleic acid anhydride, maleic acid, fumaric acid or mixtures of these compounds. In another embodiment of the process according to the invention, the impurities are polymerization inhibitors such as, for example, phenothiazine, hydroquinone monomethyl ether or hydroquinone, which are added in the production of (meth)acrylic acid, in order to prevent a formation of (meth)acrylic acid polymers during the synthesis process and the thereuponfollowing purification process.

If the impurity is maleic acid anhydride, the separation of the maleic acid anhydride from the composition may occur in that in process step a) maleic acid anhydride is hydrolyzed to at least about 50%, such as at least about 75%, such as at least about 96% and such as at least about 99.99% to form maleic acid, whereby maleic acid and/or fumaric acid precipitate in crystalline form from the composition.

It was noticed that from compositions comprising (meth) acrylic acid and maleic acid anhydride, the maleic acid anhydride can be separated in a simple way by hydrolysis and the formation of maleic acid resulting therefrom (which depending on the circumstances can at least partially convert to fumaric acid in a slow isomerization), since maleic acid (and also fumaric acid) are less soluble in (meth)acrylic acid compared to maleic acid anhydride. It was also noted here, by means of intensive experiments on compositions with a different ratio of amounts of (meth)acrylic acid, maleic acid anhydride and water, that hours or even days can pass until a precipitation of maleic acid anhydride or of maleic acid and/ or fumaric acid arising from the hydrolysis of the maleic acid anhydride can be observed.

In order to ensure as complete a hydrolysis of the anhydride as possible, for a sufficient separation of the maleic acid anhydride, it is exemplary according to the invention that the hydrolysis of the maleic acid anhydride in process step a) occurs over a time period in a range from about 1 to about 250 hours, such as over a time period from about 2 to about 100 hours and such as over a time period from about 5 to about 50 hours and, in one aspect, at a temperature in a range from about −70° C. to about 130° C., such as in a range from about −30° C. to about 100° C. and such as in a range from about −10° C. to about 20° C. The duration of the hydrolysis process is dependent on different factors, such as, for example, the temperature of the composition, the relative amount ratios of the individual components (water, (meth)acrylic acid, other impurities) in the composition, as well as on the presence of catalysts, which accelerate the hydrolysis of maleic acid anhydride. The skilled person will determine the necessary duration of the hydrolysis process by appropriate routine experiments, in which the progress of the hydrolysis in the composition is checked by sampling, for example by the determination of the water content (this decreases with increasing hydrolysis).

In one aspect, in the case of maleic acid anhydride as impurity to be separated, the controlled hydrolysis of the impurity occurs in that it is ensured that, depending on the pH-value of the composition and on the concentration of the maleic acid anhydride contained in the composition, an amount of water which is sufficient for the scale of the hydrolysis required is comprised in the composition. Thus, the composition comprises the water, for example, in an amount in a range from about 0.01 to about 50 wt %, such as in an amount in a range from about 0.1 to about 20 wt %, such as in a range from about 1 to about 10 wt % and such as in a range from about 2 to about 5 wt %, respectively based on the total weight of the composition. In another aspect, in the composition, the amount of water is, however, limited in that at most about 10 wt %, such as at most about 5 wt %, such as at most about 1 wt % and such as at most about 0.1 wt % of the maleic acid, respectively based on the weight of the maleic acid in the composition, is present in the form dissolved in water, whereby these respective maximum amounts of water depend on the temperature of the composition.

In another embodiment of the process according to the invention, the composition comprises water in such an amount that the maleic acid anhydride comprised in the composition is hydrolyzed to at least about 50%, such as to at least about 75%, such as at least about 96% and such as at least about 99% to form maleic acid and/or fumaric acid. Here, the skilled person will determine the necessary amounts of water by means of simple trials, in which the amount of maleic acid anhydride in the composition and thus the progress of the hydrolysis is determined.

If in the exemplary process according to the invention, in which maleic acid anhydride as impurity should be separated, in process step a) a composition is used which already has the necessary amount of water, in the equilibrium state, the necessary degree of hydrolysis will be reached and the maleic acid and/or fumaric acid crystallized out of the composition. If, however, the amount of water comprised in a composition is not sufficient to enable the necessary degree of hydrolysis after appropriate delays, it is exemplary according to the invention to add to the composition an amount of water such that in the equilibrium state the desired degree of hydrolysis is reached and thus the maleic acid and/or fumaric acid are caused to precipitate. In addition to the addition of water, however, the necessary degree of hydrolysis can also be adjusted by addition of catalysts, which accelerate the hydrolysis of maleic acid anhydride, such as, for example, inorganic or organic acids, or by a variation of other process parameters such as, for example, an increase in the temperature of the composition. In the case of a use of catalysts, these may be used in an amount in a range from about 1 to about 10,000 ppm, such as in a range from about 10 to about 5,000 ppm and such as in a range from about 100 to about 1,000 ppm, respectively based on the total amount of maleic acid anhydride in the composition.

If the purification of the composition comprising (meth) acrylic acid and maleic acid anhydride as impurity occurs discontinuously, in that, for example, the composition is stored in a container, the composition may then be stored in this container for the above-mentioned time period and then conducted to an appropriate device for separation of the precipitated maleic acid and/or fumaric acid, for example a filter. If the purification of the composition comprising (meth) acrylic acid and maleic acid anhydride occurs continuously, in that, for example, the composition is transferred by means of suitable crystallizers into a crystal suspension, and this crystal suspension is then separated in wash columns into (meth)acrylic acid crystals and a mother liquor, a sufficient hydrolysis of the maleic acid anhydride remaining in the mother liquor can be ensured, for example, in that the mother liquor is conducted in the cycle for a sufficiently long time by means of partial conducting back into the crystallizer.

Thus according to the invention, impurities, such as, for example, maleic acid or maleic acid anhydride are not held in solution, as described in WO-A-00/45928, but are precipitated from the composition, whereby in the case of maleic acid anhydride as impurity to be separated, this precipitation occurs by the controlled hydrolysis of the maleic acid anhydride. Since in the separation of maleic acid anhydride as impurity, compared to in the process described in WO-A-00/45928, at most small additions of water are necessary to this end, the process according to the invention enables in particular the targeted separation of maleic acid anhydride from a composition comprising (meth)acrylic acid, without decisively diluting this composition with water, and thus making more difficult a further crystallization of (meth)acrylic acid from this composition carried out in subsequent purification steps.

The separation of the maleic acid and/or of the fumaric acid in process step b) can be carried out by means of any process, which allows a separation of solid and liquid materials. For example, the separation of the crystallized maleic acid and/or of the crystalline fumaric acid occurs by filtration, sedimentation or centrifugation.

In one embodiment of the process according to the invention, the composition comprising (meth)acrylic acid and the impurities according to process step a) is the bottom product S2, which is obtained in that the aqueous (meth)acrylic acid solution, such as acrylic acid solution, obtained as quench phase is distilled in a first distillation step in the presence of an entrainer, such as in the presence of toluene, in order to remove the water from the quench phase. The (meth)acrylic acid-comprising bottom product S1 obtained in this first distillation step, which is water-poor compared to the quench phase, is distilled in a second distillation step, in order to separate low-boiling components, such as, for example, acetic acid. In this second distillation step, the (meth)acrylic acid-comprising bottom product S2 (=impure crude (meth) acrylic acid stream) is obtained. The separation of maleic acid anhydride, maleic acid or fumaric acid from the bottom product S2 can thus occur even before (meth)acrylic acid present in the bottom product S2 is separated, for example, by means of crystallization. It is also conceivable to first separate (meth) acrylic acid present in bottom product S2 by means of crystallization, and to separate maleic acid, maleic acid anhydride or fumaric acid from the thus retained mother liquor. The mother liquor can then be conducted to subsequent purification steps for the purpose of a further separation of (meth) acrylic acid, which is still present.

In another embodiment of the process according to the invention, the composition comprising (meth)acrylic acid and the impurities according to process step a) is I. The (meth)acrylic acid crystals, such as the at least partially melted (meth)acrylic acid crystals, or the mother liquor, which is obtained in step B or in step D or II. the crystal suspension, which is obtained in step A or step C of a process, which comprises the following process steps:

A) crystallization of (meth)acrylic acid from an impure crude (meth)acrylic acid stream, such as from the bottom product S2, from a process for production of (meth)acrylic acid, such as with formation of a crystal suspension by means of a first suspension generator;

B) separation of the (meth)acrylic acid crystals from the crystal suspension, such as by means of a first separating device, such as a first wash column, whereby a mother liquor is retained; as well as optionally C) renewed crystallization of (meth)acrylic acid from the first mother liquor obtained from step B), such as with formation of a second crystal suspension by means of a second suspension generator;

D) separation of the (meth)acrylic acid crystals obtained in step C) from the second crystal suspension, such as by means of a further separating device, such as at a further wash column, whereby a second mother liquor is retained.

According to the invention, by the term "mother liquor" in this text, all phases should be understood which are not present in crystalline form. In the case of a crystalline suspension by the term "mother liquor" is thus understood any liquid phase, which is retained on separation of the crystals from the crystal suspension.

The impure crude (meth)acrylic acid stream used in this particular embodiment of the process according to the invention in process A) may be based on ($\alpha$1) (meth)acrylic acid in an amount in a range from about 50 to about 99.9 wt %, such as in a range from about 60 to about 99.6 wt % and such as in a range from about 90 to about 99.5 wt %, ($\alpha$2) water, in an amount in a range from about 0.01 to about 50 wt %, such as in range from about 0.03 to about 10 wt % and such as in an amount in a range from about 0.05 to about 1 wt %, ($\alpha$3) maleic acid anhydride in a total amount in a range from about 0.01 to about 5 wt %, such as in a range from about 0.05 to about 1 wt % and such as in an amount in a range from about 0.1 to about 0.5 wt %, as well as ($\alpha$4) further impurities in an amount in a range from about 0.01 to about 5 wt %, such as in a range from about 0.03 to about 1 wt % and such as in an amount in a range from about 0.05 to about 0.5 wt %, whereby the total amount of components ($\alpha$1) to ($\alpha$4) is 100 wt %.

To the further impurities ($\alpha$4) belong, in the case of the production of acrylic acid, acrolein, acetic acid, propionic acid, aldehydes such as, for example, formaldehyde, furfural and benzaldehyde and protoanemonin, as well as polymerization inhibitors such as, for example, HQME (hydroquinone monomethyl ether), HQ (hydroquinone) and phenothiazine, which are added in the further distillative purification of the reaction products obtained in the catalytic gas phase oxidation of propylene, in order to prevent the polymerization and the therefrom resulting formation of acrylic acid dimers or acrylic acid oligomers. In the case of the production of methacrylic acid, the further impurities ($\alpha$4) are, for example, hydroxy-iso-butanoic acid, iso-butanoic acid, methacrylamide, methyl methacrylate, methacrolein, acetic acid, acrylic acid, propionic acid, HQME and HQ.

In a case of a two-step purification process (process step A to D), it is exemplary according to one embodiment of this process that already in process step A a crude (meth)acrylic acid is used which has been previously conducted into the head of the separating device use in process step D, in order to guide in this way the product crystals abraded as crystal suspension in the second process step into the suspension generator of process step A. This variant has the energetic advantage of being able to dispense with a melting in the second step and of not having to freeze out again the crystals present now in the first step.

In another embodiment of the process according to the invention, in which one of the compositions I or II is used in process step a), the crystallization is carried out as multi-step, such as two-step crystallization (process steps A to D). Multi-step processes are here operated according to the counter current flow principle, in which after the crystallization, in every step, the crystallizate is separated from the mother liquor and the mother liquor is conducted into each step at lower temperature.

The crystallization process used for the crystallization in step I and the separating process used for the separation in step II correspond to those crystallization and separating processes that are described in WO 99/14181 A1.

In particular in the case of the separation of maleic acid anhydride as impurity by means of the above-described controlled hydrolysis of the maleic acid anhydride to form maleic acid and/or fumaric acid, suspension crystallization processes may be used and in particular those suspension crystallization processes which allow a continuous design of the process according to the invention. The suspension crystallization can be carried out in a stirrer vessel crystallizer, in a scratch crystallizer, in a cooled plate crystallizer, in a crystallizing screw, in a drum crystallizer, in a pipe bundle crystallizer or the like. Particularly exemplary here are, in turn, such crystallizers which can be operated continuously. These may be the cooled plate crystallizers or scratch coolers (see the dissertation of Poschmann on suspension crystallization of organic melts and post-treatment of the crystals by sweating or washing, Diss. University of Bremen, Shaker Verlag, Aachen 1996). In one aspect, for crystallization, a scratch cooler is used.

In one aspect, the temperature of the melt during the crystallization lies between about −30 and about +14° C., such as between about −15 and about +14° C. The solid content in the crystallizer lies between about 0 and about 85 g, such as between about 20 and about 40 g solid/100 g of the composition.

The separation of the (meth)acrylic acid crystals from the crystal suspensions obtained in process steps A and C may occur by means of wash columns. In one embodiment of this process according to the invention, the suspension is supplied to a hydraulic wash column in the upper part of the column. The mother liquor is discharged from the column by means of a filter, whereby a densely packed crystal bed forms. The crystal bed and the mother liquor flow in the direction of the floor of the wash column.

At the floor of the column is located a moved, such as rotating scratch device or scratcher, which generates a suspension again from the densely packed crystal bed. This suspension may be pumped and melted by means of a melter, such as a heat exchanger. A part of the melt can, for example, serve as wash melt; this is then pumped back into the column and in one-aspect washes the crystal bed migrating in opposing direction, i.e. the crystallized (meth)acrylic acid is washed in the counter-flow of the conducted-back (meth)acrylic acid. The wash melt effects on the one hand a washing of the crystals, on the other hand the melt at least partially crystallizes on the crystals. The enthalpy of crystallization being released warms the crystal bed in the washing region of the column. In this way, a purification effect analogous to the sweating of the crystals is achieved. In this context, reference is made to DE 102 42 746 A1 as well as DE 101 49 353 A1 with regard to the separation of (meth)acrylic acid crystals from crystal suspensions.

In one embodiment of this process according to the invention for production of (meth)acrylic acid, in which merely a one-step purification process is carried out (process steps A and B), at least a part of the mother liquor obtained in step B is conducted back to step A. In this way the mother liquor can be conducted in a cycle. In an intended separation of maleic acid anhydride as impurity to be separated, thus, the extent of hydrolysis of maleic acid anhydride can be influenced, in addition to by the amount of water in the composition, also by the regulation of the amount of mother liquor which is conducted back to step A, and thus by the residence time of the mother liquor in the exemplary continuous purification process.

It is also conceivable to conduct at least a part of the (meth)acrylic acid crystals obtained in process step B to process A for inoculation in crystalline form, as is likewise described in DE 102 11 686 A1.

If this process according to the invention is operated with a two-step purification (process stages A to D), according to one aspect of the invention, the (meth)acrylic acid crystals obtained in process step B and/or in process step D in crystalline and/or at least partially melted form or the mother liquors obtained in process steps C and D are at least partially conducted back to one of process steps A to D, whereby the exact type of conducting back of the crystalline or melted (meth)acrylic acid or of the mother liquors in the case of a two-step purification process is described in DE 102 11 686 A1. The particular embodiments described there in the case of a two-step purification process are also exemplary in the case of the process according to the invention for production of (meth)acrylic acid, which comprises a purification process with the process steps A to D.

If, in the process according to the invention, the mother liquor separated in process step B or in process step D as composition comprising (meth)acrylic acid and impurities is used according to process step a), the mother liquor is at least partially directly conducted to the corresponding separating device for separation of the impurities according to the process b), for example for a filter.

If, in the process according to the invention, the (meth)acrylic acid crystals obtained in process step B or in process step D as composition comprising (meth)acrylic acid and impurities is used according to process step a), it is exemplary according to the invention that the (meth)acrylic acid crystals are conducted at least partially melted and in melted form to the device for separation of the impurities, in order to keep as low as possible a separation of (meth)acrylic acid crystals in the separating device for separation of impurities and thus a loss of yield. The separation of the impurities from a melted (meth)acrylic acid can be achieved in that in the case of a partial melting of (meth)acrylic acid crystals and conducting back of these melted (meth)acrylic acid crystals into one of the process steps A to D to achieve a good purity of the (meth)acrylic acid (see above details in connection with the process described in DE 102 11 686 A1) this stream of melted (meth)acrylic acid is conducted either directly or with help from a separate product cycle through the separating device for separation of the impurities.

If, in the process according to the invention, the crystal suspension obtained in process step A or in process step C is used as composition comprising (meth)acrylic acid and impurities according to process step a), it is exemplary according to the invention that the crystal suspension obtained in these process steps is conducted at least partially melted and in molten form through the separating device for separation of impurities. Then, the melted crystal suspension can be conducted again to the crystallizer.

In the case of a one-step purification process (process steps A and B), as composition comprising (meth)acrylic acid and impurities, such as maleic acid anhydride, according to process step a), a composition may be used selected from:
(1) the mother liquor, which was obtained in process step B, in so far as this is at least partially conducted back to process step A;
(2) the at least partially melted (meth)acrylic acid crystals, which were obtained in process step B;
(3) the at least partially melted crystal suspension, which was obtained in step A.

In addition to a separation of impurities from only one of the compositions (1), (2) or (3), in the case of a one-step purification process, a separation of the impurities at more than one position of the purification process or from more than one, different, compositions can, of course, occur. It is thus conceivable to separate the impurities both from the mother liquor (composition (1)) as well as from the partially melted (meth)acrylic acid crystals (composition (2)). A separation from all compositions (1) to (3) is also possible. An example is a separation from the mother liquor that was obtained in process step B, in so far as this is at least partially conducted back into process A.

In the case of a two-step purification process (process step A to D), as composition comprising (meth)acrylic acid and impurities according to process step A, a composition may be used selected from:
(4) the mother liquor, which was obtained in process step B and conducted to process step C;
(5) the mother liquor, which was obtained in process step B and at least partially conducted back into process step A;
(6) the mother liquor, which was obtained in process step D in so far as this mother liquor is at least partially conducted back, such as into process step C;
(7) the at least partially melted (meth)acrylic acid crystals, which were obtained in process B;
(8) the exemplary at least partially melted (meth)acrylic acid crystals, which were obtained in process step D and which are conducted back at least partially into process A;
(9) the crystal suspension, such as the at least partially melted crystal suspension, which was obtained in step A;
(10) the crystal suspension, such as the at least partially melted crystal suspension, which was obtained in step C;
(11) the crude (meth)acrylic acid, which is used in process step A and which was previously conducted into the head of the second wash column.

Also with regard to this two-step purification process, a separation of impurities can occur not only from one of the compositions (4) to (11), but also from at least two, such as at least three and such as at least four of these compositions, whereby a separation from composition (8) is most exemplary, followed by a separation from composition (10), in turn followed by a separation from composition (4), and in turn followed by a separation from composition (5) and in turn followed by a separation from composition (7).

If the impurity, which is separated in process step b) from one or more of the compositions (1) to (11), is maleic acid anhydride, it should be ensured in the process according to the invention that the compositions comprise sufficient amounts of water in order to ensure a sufficient hydrolysis of the maleic acid, in a continuous purification process, in which separated mother liquor and/or separated (meth)acrylic acid crystals are at least partially conducted back to one of the process steps A or B (or, in a process with two-step purification process, to one of the process steps A to D). If a composition does not comprise enough water for a satisfactory separation of the maleic acid anhydride, in the process according to the invention, water can additionally be introduced. The water can already be added before process step A to the impure crude (meth)acrylic acid stream from a process for production of (meth)acrylic acid and used in process step A. The increase of the amount of water in this composition has an effect, in a continuously operating purification process, on the water content of all other compositions (1) to (6) and (8) to (11), so that the extent of crystallization of maleic acid and/or fumaric acid in these compositions can be regulated by means of the water content of the starting composition used in process step A. It is also conceivable to add the water directly to the individual compositions (1) to (11).

In addition to influencing the extent of hydrolysis of the maleic acid anhydride by means of the amount of water in the composition, this can also be regulated over time, in that the maleic acid anhydride in a continuous purification process is conducted in the cycle by the conducting back of mother liquor and/or (meth)acrylic acid. This duration is, in turn, dependent on the relative amounts in which the mother liquor or the optionally melted (meth)acrylic acid crystals are conducted back into the individual process steps. The skilled person will determine the individual process parameters that are necessary for a satisfactory precipitation of maleic acid and/or fumaric acid from the compositions, by means of simple routine experiments.

The present invention also relates to a device for production of acrylic acid, comprising, as components connected together in fluid-conducting fashion, an acrylic acid reactor, a quench tower, a distillation device and a purification device, which comprises a separation device for separation of impurities, which comprises the features ($\epsilon 1$) to ($\epsilon 5$):
($\epsilon 1$) the device unit comprises a crystallization region, for example comprising a crystal suspension generator, a separating region, for example comprising a wash column, a separating device, at least two guides as well as optionally at least one melter;
($\epsilon 2$) the crystallization region comprises at least one inlet $\epsilon 2E\_1$ and one outlet $\epsilon 2A\_1$, whereby the outlet $\epsilon 2A\_1$ is connected by means of a first guide with an inlet $\epsilon 3E\_1$ of the separating region $\epsilon 3$;
($\epsilon 3$) the separating region comprises at least inlet $\epsilon 3E\_1$ and at least one outlet $\epsilon 3A\_1$, whereby the inlet $\epsilon 3E\_1$ of the separating region $\epsilon 3$ is connected by means of the first guide with the outlet $\epsilon 2A\_1$ of the crystallization region and the outlet $\epsilon 3A\_1$ is connected with a second guide for the mother liquor separated in the separating region;
($\epsilon 4$) the melter comprises an inlet $\epsilon 4E$ and an outlet $\epsilon 4A$, whereby the inlet $\epsilon 4E$ of the melter is connected by means of a third guide with a further outlet $\epsilon 3A\_2$ of the separating region for the removal of separated (meth)acrylic acid crystals and the outlet $\epsilon 4A$ by means of a fourth guide with a further inlet $\epsilon 3E\_2$ of the separating region for the conducting back of melted (meth)acrylic acid crystals into the separating region, or whereby the inlet $\epsilon 4E$ of the melter is connected by means of a fifth guide with a further outlet ε3A_2 of the crystallization region for the removal of a crystal suspension and the outlet ε4A by means of a sixth guide with a further inlet ε2E_2 of the crystallization region;

(ε5) through the separating device is conducted the second guide, the fourth guide or the sixth guide, whereby, in one aspect, the second, the fourth or the sixth guide is conducted through the separating device in such a way that the separation of crystallized impurities from the compositions conducted in the second, fourth or sixth guide is enabled.

According to one embodiment of the invention, the separating device (ε5) is a filter, a centrifuge, a sedimentation device or hydrocyclone, whereby a filter is exemplary. As filter, all filters can be used which make it possible to separate impurities precipitated from a composition discontinuously or continuously, such as continuously. In this context, exemplary continuously working filters comprise in particular gravel or sand filters, suction filters, candle filters, leaf filters such as circular or axial leaf filters, centrifugal disc filters such as, for example, wash filters or residue filters, filter presses. Exemplary continuously operating filters comprise in particular rotary filters, such as, for example, vacuum rotary filters, pressure rotary filters or drum filters, rotation pressure filters, in particular such which operate according to the principle of dynamic cross-flow filtration, belt filters such as, for example, vacuum belt filters, belt cell filters, capillary belt filters or paper mat belt filters.

The filters used in the process according to the invention can comprise packed bed as well as layer filters. As materials for the packings or the layer filter, all materials known to the skilled person can be used which have a sufficient resistance to a chemical attack by, above all, (meth)acrylic acid.

In this context, it is exemplary that in the case of a use of a layer filter this is a filter comprising a sieve, such as a sieve made of stainless steel, which has a mesh size in a range from about 0.1 to about 10,000 µm, such as in a range from about 10 to about 1,000 µm and such as in a range from about 100 to about 500 µm.

In an embodiment of the device according to the invention, it comprises two of the above-mentioned purification device, whereby these two purification devices are connected with each other in fluid-conducting fashion in such a way that the second guide, which is connected with the outlet ε3A_1 of the separation region of the first purification device, leads into the inlet ε2E_1 of the crystallization device of the second purification device, whereby the separating region of the second purification device, by means of a seventh guide, with which in the separating region of the second purification device, separated (meth)acrylic acid crystals can be removed from the separating region of the second separation device and conducted into the crystallization region of the first purification device.

The present invention further relates to the use of the above-described device, of the above-mentioned purification device and of the above-mentioned process for production of (meth)acrylic acid, such as for production of acrylic acid, which has a purity of more than about 90 wt. %, such as more than about 95 wt % and such as more than about 99.5 wt %, respectively based on the acrylic acid with impurities.

The invention also relates to the (meth)acrylic acid obtainable by the above-mentioned process.

The present invention further relates to (meth)acrylic acid, whereby the (meth)acrylic acid has a maleic acid anhydride content of less than about 50 ppm, such as less than about 10 ppm and such as less than about 1 ppm.

The present invention also relates to water-absorbing polymers that are obtainable by polymerization of the above-mentioned acrylic acid.

The present invention finally relates to the use of these water-absorbing polymers or of the above-mentioned (meth)acrylic acid, in particular of the above-mentioned acrylic acid, in fibers, sheets, foams and composites as well as fibers, sheets, foams and composites which comprise the above-mentioned water-absorbing polymers or the above-mentioned (meth)acrylic acid, in particular the above-mentioned acrylic acid.

The present invention is more closely illustrated by means of non-limiting figures.

Figure 1:
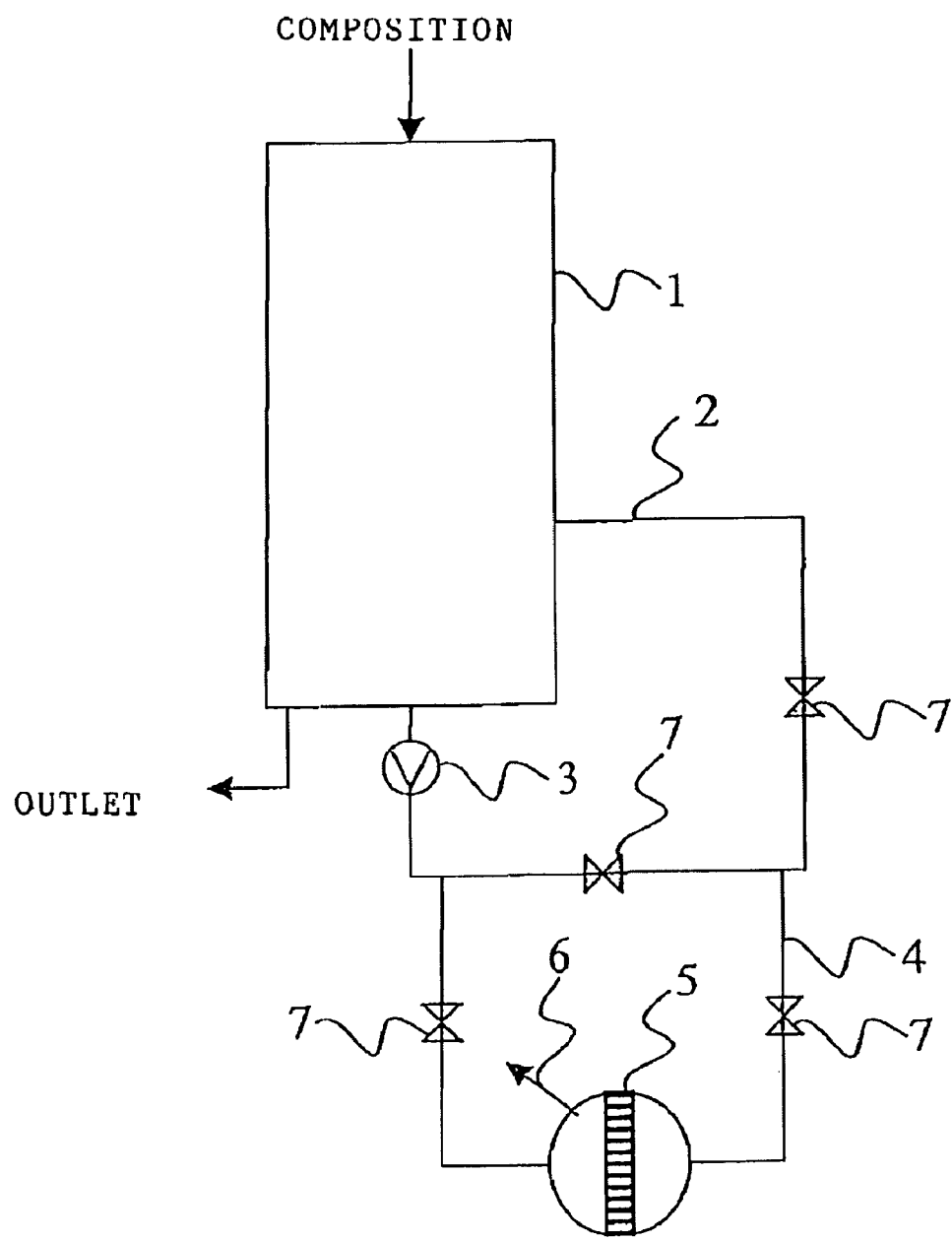
FIG. 1 shows the basis solution of the process according to the invention, in which crystallized impurities are separated continuously from a composition stored in a container.

According to the basis solution of the process according to the invention depicted in FIG. 1, a composition comprising (meth)acrylic acid and impurities, in particular maleic acid anhydride, and stored in a stock container 1, is stored for so long until a sufficient hydrolysis of the maleic acid anhydride has occurred. In the case of a continuous crystallization process for purification of (meth)acrylic acid, the stock container 1 corresponds to a suspension generator, to a wash column or to a supply line or discharge line for a crystal suspension, for crystallized (meth)acrylic acid separated from the crystal suspension, or for mother liquor, depending on from which composition the crystallized impurities, in particular the crystallized maleic acid and/or fumaric acid, are separated.

By means of a product cycle 2, the composition is removed continuously or discontinuously from the stock container 1, whereby the product cycle is operated by means of a product cycle pump 3. From the product cycle 2, by means of a further product cycle 4, the composition is conducted through the separating device, in which crystallized impurities, in particular crystallized maleic acid and/or fumaric acid are separated by means of discharge 8. The composition freed from the crystallized impurities is then conducted back into the product cycle 2 and, via this, then into stock container 1. Besides the procedure depicted in FIG. 1, it is also possible to conduct the composition conducted in product cycle 2 directly (and not by means of the separate product cycle 4), through the separating device 5.

Figure 2A:
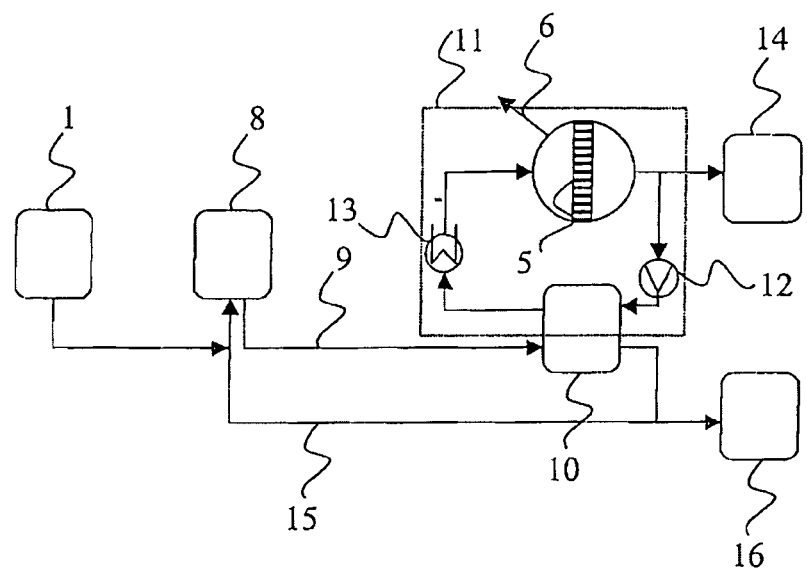
FIG. 2A shows the process course of a process according to the invention, in which, in a one-step purification process, impurities are separated from melted (meth)acrylic acid, which were obtained after separation from a crystal suspension.

FIG. 2A shows the process course of a process according to the invention, in which, in a one-step purification process, impurities are separated from the at least partially melted (meth)acrylic acid, which was obtained after the separation in the wash column 10.

Figure 2B:
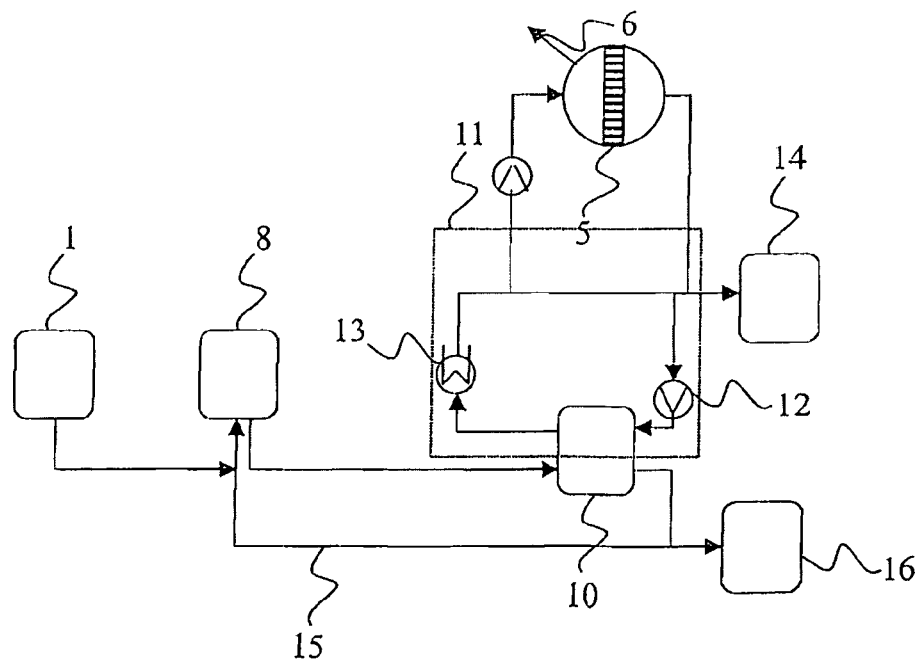
FIG. 2B shows the process course depicted in FIG. 2A, whereby, however, the separation of the impurities does not occur directly within the product cycle, but by means of a separate cycle which is connected with the product cycle.

The composition stored in stock container 1 and comprising (meth)acrylic acid and impurities is conducted to a crystal suspension generator 8. The formed crystal suspension is then conducted by means of a feed 9 into a separating device (e.g. a wash column) 10. In the separating device 10, the (meth) acrylic acid crystals are separated from the mother liquor. In addition, a part of the (meth)acrylic acid crystals are transferred again into a crystal suspension and this crystal suspension conducted in a product cycle 11 driven by means of a product cycle pump 12, in which product cycle 11 the (meth) acrylic acid crystals are melted by means of a heat exchanger 13 and, for increase of the purity of the (meth)acrylic acid, at least partially conducted back as wash liquid to the counterflow wash in the wash column 10. Thus, the wash column 10 serves to separate solid and liquid as well as to carry out a displacement washing, whereby the displacement washing is carried out without loss of wash fluid. The other part of the (meth)acrylic acid crystals leaves the system and flows into the product container 14 (if the purity of the (meth)acrylic acid obtained by means of the one-step purification process shown in diagram 2A is not sufficient, the (meth)acrylic acid crystals can be conducted to a further purification step). The at least partially melted (meth)acrylic acid crystals are conducted through the separation device for separation of impurities 5. According to FIG. 2B, the at least partially melted (meth)acrylic acid crystals can also be conducted to the separating device by means of a separate product cycle. The separated impurities are removed via discharge line 6 and the composition freed from the impurities is conducted back into the separating device 10. In one embodiment of this one-step purification process, at least a part of the mother liquor separated in wash column 10 is conducted back via feed 15 into the suspension generator 8, the other part of the mother liquor is conducted as effluent into the mother liquor container 16.

Figure 2C:
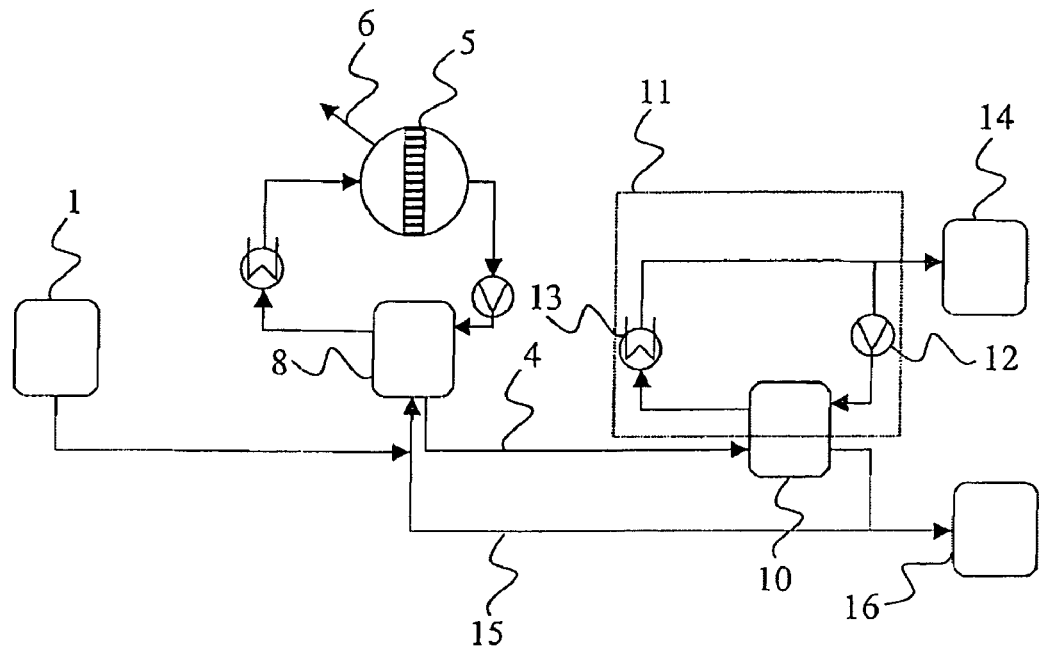
FIG. 2C shows the process course of a process according to the invention, in which in a one-step purification process impurities are separated from the crystal suspension, which was obtained in the crystallizer and which is, by means of a product cycle, at least partially melted and conducted back into the crystallizer.
Figure 2D:
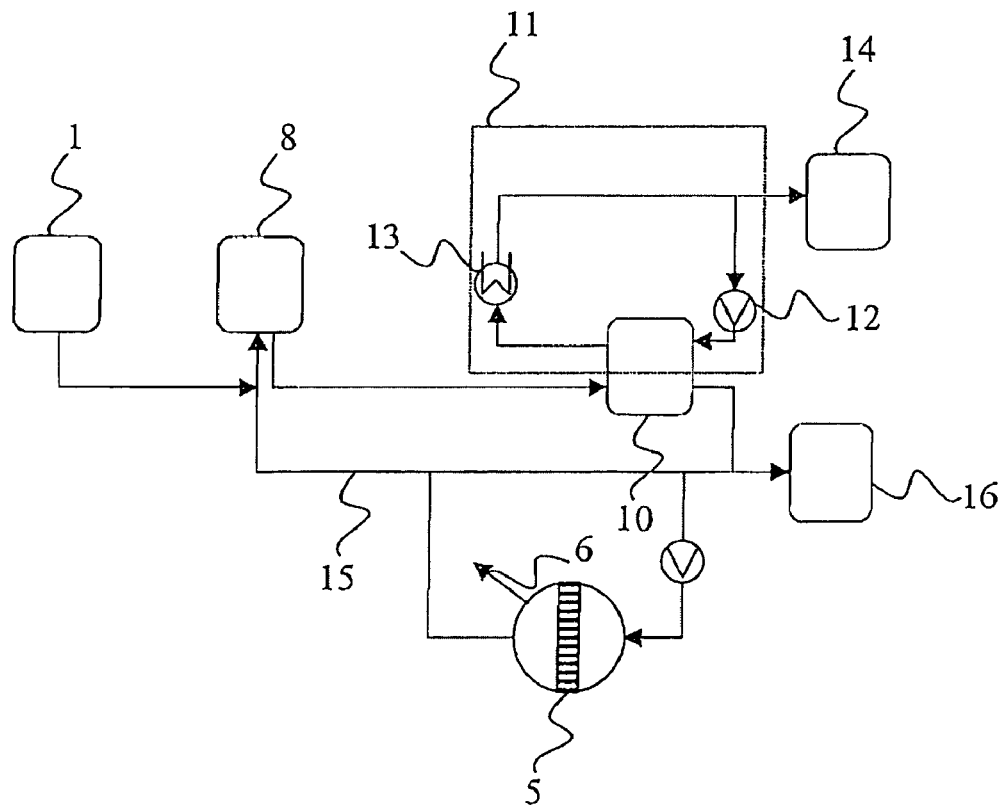
FIG. 2D shows the process course of a process according to the invention, in which, in a one-step purification process, impurities are separated from the mother liquor, which was obtained on separation of the crystallized (meth)acrylic acid in the wash column and which is at least partially conducted back into the crystallizer.

FIGS. 2C and 2D show the one-step purification process corresponding to that of FIG. 2A, whereby, however, not the at least partially melted (meth)acrylic acid crystals which were obtained after the separation in the wash column 10, but rather the crystal suspension (FIG. 2D) obtained in the suspension generator 8 or the mother liquor of the separating device 5 conducted back into the suspension generator 8 are supplied.

Figure 3:
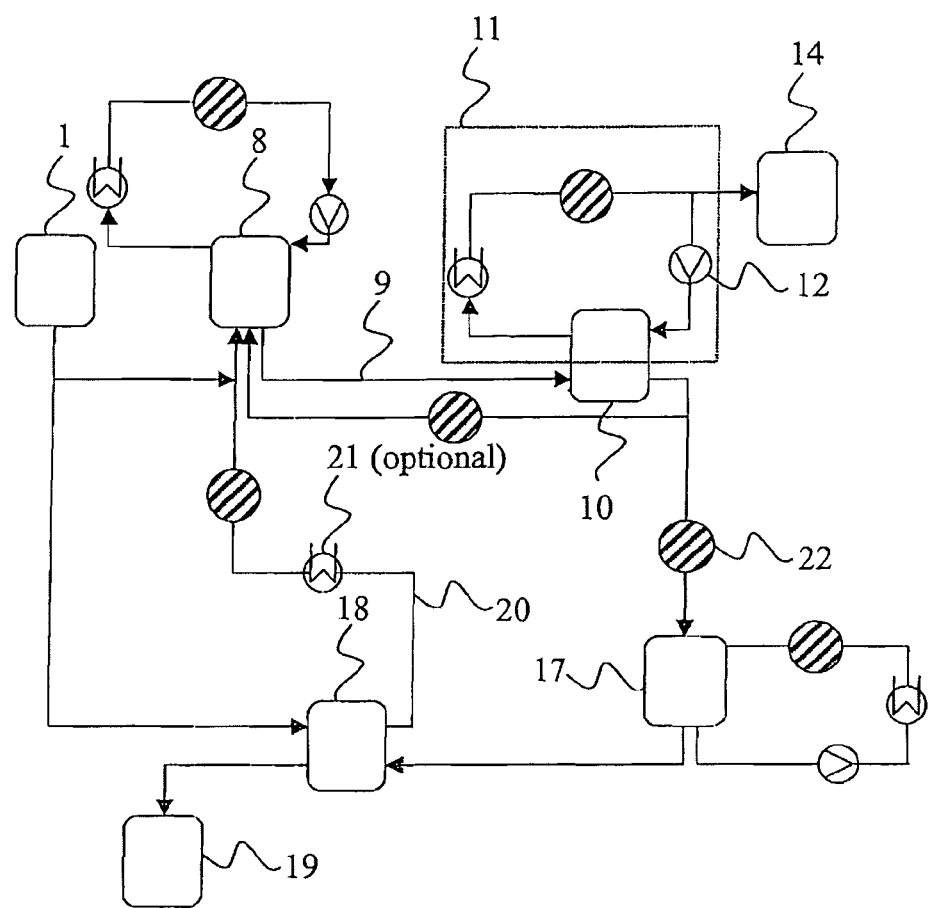
FIG. 3 shows at which positions in a two-step purification process a separation according to the invention of impurities can occur.

FIG. 3 shows a two-step purification process, in which the mother liquor separated in wash column 8 is at least partially conducted into a further suspension generator 17. The crystal suspension obtained in suspension generator 17 is conducted into a further wash column 18, in which the (meth)acrylic acid crystals are separated from the mother liquor. The (meth) acrylic acid crystals separated in this second wash column 18 are, in crystalline form or after they have been at least partially melted by means of a heat exchanger, conducted via feed line 20 to the first suspension generator. It is also exemplary in this two-step purification process that the crude (meth)acrylic acid is conducted out of the stock container 1 into the head of the second wash column, in order, in this way, to conduct the product crystals scraped off in the second process step as crystal suspension into the suspension generator of process step A. This variant has the energetic advantage of being able to dispense with a melting in the second step and not having to freeze again the crystals now present in the first step.

In FIG. 3, it is illustrated at which positions a separation of crystallized impurities, in particular of crystallized maleic acid and/or fumaric acid is possible by means of separating device 22.

The invention is now more closely illustrated by means of an example:

EXAMPLE 113.5 g of a bottom product from a column with the composition given in table 1 was placed with 1.6 g water in a Erlenmeyer flask. The mixture was allowed to stand over a time period of 42 hours at room temperature and then filtered using a vacuum filter. 108.5 g filtrate with the composition likewise given in table 1 were obtained. The solid remaining on the filter was then centrifuged at 4,000 rpm for 5 minutes, whereby 3.6 g of a solid was obtained. This solid was dissolved in 129.0 g highly pure acrylic acid, for the purpose of analysis. The composition of the solid is likewise given in table 1 (the components comprised in the compositions were analyzed by means of respectively gas chromatography and Karl-Fischer-Titration; the relative amounts of the components in the bottom product, in the filtrate and in the solid do not add up to 100 wt % exactly, because of the rounding up and rounding down of the analysis data obtained for these compositions.

TABLE 1

| Components (all entries in wt. %, unless otherwise given) | Bottom product (based on the total amount of the bottom product) | Filtrate (based on the total amount of the filtrate) | Solid (based on the total amount of the solid) |
|---|---|---|---|
| Water | 0.018 | 0.979 | 1.22 |
| MEHQ[1] | 0.0044 | 0.0037 | 0.51 |
| Hydroquinone | 0.113 | 0.125 | <800 ppm |
| Acryl acid | 88.6 | 89.0 | 48.43 |
| Acetic acid | 0.055 | 0.049 | 0.59 |
| Propionic acid | 0.036 | 0.034 | 0.48 |
| Dimeric acrylic acid | 2.759 | 2.959 | 4.79 |
| MA/MS[2] | 8.131 | 6.215 | 44.16 |
| Furfural | 0.0327 | 0.036 | <40 ppm |
| Benzaldehyde | 0.075 | 0.08 | <40 ppm |
| Acrolein | 0.001 | 0.0019 | <40 ppm |
| Protoanemonine | 0.039 | 0.0398 | <40 ppm |
| Remainder | 0.06 | 0.440 | <800 ppm |

[1]Methyl hydroquinone
[2]Maleic acid anhydride/maleic acid

The invention claimed is:

1. A process for production of (meth)acrylic acid, whereby first a crude (meth)acrylic acid is produced and this crude (meth)acrylic acid is then continuously purified, wherein the continuous purification of the crude (meth)acrylic acid comprises the following process steps:

a) in a composition comprising (meth)acrylic acid and impurities, precipitating the impurities from the composition in crystalline form wherein the impurity comprises maleic acid anhydride, and wherein the maleic acid anhydride is hydrolyzed to a portion of at least about 50 mol %, based on the total amount of the maleic acid anhydride comprised in the composition before the staff of the hydrolysis, with formation of maleic acid and/or fumaric acid, wherein maleic acid and/or fumaric acid precipitate in crystalline form from the composition;

b) separating the crystalline maleic acid and/or fumaric acid precipitated from the composition.

2. The process according to claim 1, wherein the hydrolysis of the maleic acid anhydride in process step a) occurs over a time period in a range from about 1 to about 250 hours at a temperature in a range from about 70 to about 130° C.

3. The process according to claim 1, wherein the composition is (meth)acrylic acid crystals in at least partially melted form or the mother liquor, which are obtained in step B or in step D of a process which comprises the following process steps:
- A) crystallization of (meth)acrylic acid from an impure crude (meth)acrylic acid stream from a process for production of (meth)acrylic acid with formation of a crystal suspension by means of a first suspension generator;
- B) separation of the (meth)acrylic acid crystals from the crystal suspension by means of a first separating device, whereby a mother liquor is retained; as well as optionally
- C) renewed crystallization of (meth)acrylic acid from the first mother liquor obtained from step B) with formation of a second crystal suspension by means of a second suspension generator;
- D) separation of the (meth)acrylic acid crystals obtained in step C) from the second crystal suspension by means of a further separating device, whereby a second mother liquor is retained.

4. The process according to claim 1, wherein the composition is crystal suspension in at least partially melted form which is obtained in process step A or step C of a process which comprises the following process steps:
- A) crystallization of (meth)acrylic acid from an impure crude (meth)acrylic acid stream from a process for production of (meth)acrylic acid with formation of a crystal suspension by means of a first suspension generator;
- B) separation of the (meth)acrylic acid crystals from the crystal suspension by means of a first separating device, whereby a mother liquor is retained; as well as optionally
- C) renewed crystallization of (meth)acrylic acid from the first mother liquor obtained from step B) with formation of a second crystal suspension by means of a second suspension generator;
- D) separation of the (meth)acrylic acid crystals obtained in step C) from the second crystal suspension by means of a further separating device, whereby a second mother liquor is retained.

* * * * *

UNITED STATES PATENT AND TRADEMARK OFFICE
CERTIFICATE OF CORRECTION

PATENT NO. : 7,557,246 B2  
APPLICATION NO. : 11/571877  
DATED : July 7, 2009  
INVENTOR(S) : Stefan Nordhoff et al.

Page 1 of 1

It is certified that error appears in the above-identified patent and that said Letters Patent is hereby corrected as shown below:

Column 14,
Line 62, "staff of the hydrolysis" should read -- start of the hydrolysis --.

Signed and Sealed this

Eighth Day of September, 2009

David J. Kappos
*Director of the United States Patent and Trademark Office*